United States Patent [19]

Gibson et al.

[11] Patent Number: 5,171,318
[45] Date of Patent: Dec. 15, 1992

[54] TREATED CORNEAL PROSTHETIC DEVICE

[75] Inventors: David Gibson, Irvine, Calif.; Michael Lerner, Shawnee; Robert Nordquist, Oklahoma City, both of Okla.; Cary Reich, Irvine, Calif.

[73] Assignee: Chiron Ophthalmics, Inc., Irvine, Calif.

[21] Appl. No.: 825,425

[22] Filed: Jan. 21, 1992

Related U.S. Application Data

[63] Continuation of Ser. No. 726,151, Jul. 1, 1991, abandoned, which is a continuation of Ser. No. 445,945, Dec. 8, 1989, abandoned, which is a continuation of Ser. No. 191,994, May 9, 1988, abandoned, which is a continuation of Ser. No. 117,828, Nov. 9, 1987, abandoned.

[51] Int. Cl.$^5$ .............................................. A61F 2/14
[52] U.S. Cl. ............................................ 623/5; 623/6
[58] Field of Search ......................... 623/6, 66; 427/2

[56] References Cited

U.S. PATENT DOCUMENTS

| | | |
|---|---|---|
| 2,714,721 | 8/1955 | Stone, Jr. . |
| 2,952,023 | 9/1960 | Rosen . |
| 3,438,374 | 4/1969 | Falb et al. . |
| 3,454,966 | 7/1969 | Rosen . |
| 3,959,078 | 5/1976 | Guire . |
| 3,992,563 | 11/1976 | Tanaka . |
| 4,126,904 | 11/1978 | Shepard . |
| 4,189,546 | 2/1980 | Deichert et al. . |
| 4,223,984 | 9/1980 | Miyata et al. . |
| 4,240,163 | 12/1980 | Galin . |
| 4,346,482 | 8/1982 | Tennant et al. . |
| 4,452,235 | 6/1984 | Reymolds . |
| 4,589,881 | 5/1986 | Pierschbacher ............. 623/11 |
| 4,614,517 | 9/1986 | Ruoslahti et al. . |
| 4,624,669 | 11/1986 | Grendahl . |
| 4,662,881 | 5/1987 | Norden . |
| 4,715,858 | 12/1987 | Lindstrom ................. 623/5 |
| 4,722,906 | 2/1988 | Guire . |
| 4,973,493 | 11/1990 | Guire . |
| 4,979,959 | 12/1990 | Guire . |
| 5,002,582 | 3/1991 | Guire . |

FOREIGN PATENT DOCUMENTS

| | | |
|---|---|---|
| 2705234 | 8/1978 | Fed. Rep. of Germany . |
| 544429 | 2/1977 | U.S.S.R. . |
| 700125 | 11/1979 | U.S.S.R. . |

OTHER PUBLICATIONS

Epikeratophakia in Very Young Babies, *AMO Kerato-Lens Update*, vol. 2, No. 2, Aug. 1985.
Guire et al., Stepwise-Crosslinking Agents for Photocoupling of Enzymes and Lectins to Mammalian Cells, *Glycoconjugate Research*, vol. II, 1051 (1977).

Primary Examiner—David Isabella
Assistant Examiner—D. S. Brittingham
Attorney, Agent, or Firm—Rothwell, Figg, Ernst & Kurz

[57] ABSTRACT

Prosthetic devices are prepared for subepithelial implantation by coating their surfaces with a coating comprising crosslinked or uncrosslinked fibronectin. If the surface of the device comprises a material which does not normally bind fibronectin, it is pretreated, for example, by coating with poly(L-lysine). The coated prosthetic device is implanted by removing a portion of the epithelium, affixing the coated device to the subepithelial tissue optionally replacing all or part of the removed epithelium, and allowing new epithelial tissue to grow over and affix itself to the surface of the prosthetic device. The method of the invention can be used to implant contact lenses permanently beneath the epithelium of the cornea.

7 Claims, 3 Drawing Sheets

TREATED CORNEAL PROSTHETIC DEVICE

This is a continuation of application Ser. No. 07/726,151, filed Jul. 1, 1991, now abandoned, which is a continuation of application Ser. No. 07/445,945, filed Dec. 8, 1989, now abandoned, which is a continuation of application Ser. No. 07/191,994, filed May 9, 1988, now abandoned, which is a continuation of application Ser. No. 07/117,828, filed Nov. 9, 1987, now abandoned.

BACKGROUND OF THE INVENTION

This invention relates to methods for implanting prosthetic devices in humans or animals. More particularly, it relates to a method for implanting a prosthetic device wherein it is desired to incorporate the prosthetic device permanently beneath an epithelial surface. The methods of the invention can be applied to subepithelial implantation of prosthetic devices such as contact lenses, dermal devices, dental devices otolaryngological devices, vascular access and ostomy devices. The invention also relates to methods of treating prosthetic devices and to treated devices produced thereby, which allow the devices to be implanted permanently below the epithelial layer.

There are a number of prosthetic devices which necessarily or desirably can be implanted either completely or partially beneath epithelial tissues. It is to be understood that reference to "epithelial" tissues herein includes epidermal tissue as well as other epithelial tissues. Implantation beneath the epithelium may be done for purposes of fixation of the device relative to other tissues and/or for cosmetic purposes. Examples of implanted prostheses include dental prostheses such as artificial teeth and bridgework; hearing aids; dermal implants; vascular access devices, such as those associated with hyper-alimentation; colostomy devices; and prosthetic corneas, which can be made of synthetic or naturally-derived materials. While the methods of the invention will be described specifically with reference to their application in subepithelial implantation of prosthetic corneas, it will be readily understood that they can be applied any time one desires to implant a prosthetic device partially or completely beneath a viable epithelial surface.

Advantageously, the methods of the invention can be employed in the field of ophthalmology. Ophthalmologists have long been concerned with the treatment of vision problems caused by defects in the cornea. The most common of these problems are nearsightedness, which can be caused by excessive corneal curvature; farsightedness, which can be caused by insufficient corneal curvature; and astigmatism, which is caused by corneal asymmetry. Traumatic injury to the cornea with resultant scarring and/or distortion of corneal tissue, can also cause vision problems. Frequently, corrective lenses such as eyeglasses or contact lenses can be employed to correct common vision problems. In certain severe conditions, however, or where there has been damage to the cornea, or in the case of contact lens intolerant patients, surgical procedures must be employed to correct the geometry of the cornea. Although a number of these surgical procedures, known generally as refractive keratoplasties, have been developed, consistently good results have not been obtained. Consequently, these procedures have not been widely employed.

A number of refractive keratoplasty procedures employ the implantation of geometrically altered corneal tissue obtained from donor corneas or from the patient's own cornea to obtain refractive correction. In one such procedure an anterior portion of the patient's own cornea is removed. The removed corneal section is reshaped on a cryolathe in order to reduce or increase the amount of curvature. The cornea is then allowed to thaw and it is stitched back into place on the corneal surface. In another procedure, a donor cornea that has been shaped on a cryolathe is used to replace an anterior portion of the patient's cornea that has been surgically removed.

In another refractive keratoplasty procedure, only the epithelial layer of the patient's cornea is removed. A donor lens "button" that previously has been frozen and ground to the desired degree of refraction, is then sewn in place.

U.S. Pat. No. 4,346,482, issued to Tennant et al., describes a method for correcting vision in which a circular portion of a donor cornea is anteriorly shaped for refractive correction of the patient's vision. The posterior surface of the corneal section is ground to correspond to the curvature of the patient's cornea. The lens includes a posteriorly directed integral ring which is inserted into the patient's cornea. The donor cornea is preserved by a freezing process which kills keratocytes, such that only collagen is left for fixation. The procedure relies on migration of keratocytes from the patient's tissues into the donor cornea for healing and incorporating the donor cornea into the eye.

All of the foregoing procedures, which use donor corneas or the patient's own corneal tissue, rely on extremely precise and delicate cutting procedures. Even using sophisticated equipment that is available for this purpose, it is difficult to assure the required degree of refractive correction. Where donor corneas are to be used, the supply of donor corneas is extremely limited, due to social and religious mores which make it difficult to obtain corneas from cadavers. In the event that these procedures fail, for example, because of tissue rejection, infection, improper healing or inadequate refractive correction, it may be difficult to obtain additional biocompatible material to perform corrective surgery. Yet another drawback to these procedures is the inherent difficulty of working with biological materials, which have a limited useful lifetime and require special handling procedures to keep them in viable condition.

A number of refractive keratoplasty procedures have been developed which employ corneal prostheses made from synthetic materials or from non-living materials derived from natural sources such as collagen. U.S. Pat. No. 4,581,030, issued to Bruns et al., discloses a prosthetic replacement for the cornea, particularly a transparent collagen material useful for making such a prosthesis and to methods for making the transparent collagen material. The prosthetic cornea comprises collagen, polyhydroxyethylmethacrylate or vitrosin.

U.S. Pat. No. 3,454,966, issued to Rosen, discloses a corneal transplant structure of synthetic material compatible with body tissues as a replacement for a removed section of the cornea. The outer marginal portion of the structure is in intimate contact with the marginal rim of the cornea surrounding the structure. A controlled temperature is applied to the structure around the area of its contact with parts of the cornea to facilitate attachment.

A number of papers have been published which describe the use of tissue adhesives such as cyanoacrylate adhesives to "glue" synthetic contact lenses onto the corneal surfaces (see, e.g., Richards, J. S., *Can J Ophthalmol.*, 6(2):98–103 (1971); Ruben, M., *Trans. Ophthalmol. Soc. U.K.*, 90:551–564 (1970); Dohlman, C. H., *Arch. Ophthalmol.*, 83(1):10–20 (1970); Dohlman, C. H., *Trans. Am. Acad. Ophthalmol. Otolaryngol.*, 73(3):482–493 (1969)). The synthetic lenses are generally made of acrylate polymers such as polyhydroxyethylmethacrylate.

The aforementioned procedures, in which synthetic or collagen contact lenses are affixed to the corneal surface, overcome some of the previously discussed problems inherent in keratoplasty using donor corneas or the patient's own corneal tissue. Difficulties are encountered with synthetic lenses, however, inasmuch as it is difficult to assure that they will be permanently incorporated into the patient's eye without infection or rejection. One procedure which has been proposed to overcome this problem involves making an incision in the stromal tissues of the cornea to form a pocket into which a synthetic lens is placed. This procedure has been successfully used to increase refractive power in rabbits (McCarey, B. E. and Andrews, D. M., *Invest. Ophthalmol. Vis. Sci.*, 21:107–115 (1981)). In primates, however, the Bowman's membrane, which is relatively rigid, causes the cornea to resist any increase in curvature induced by the implanted lens. Koenig and co-workers attempted to correct this problem by making a series of relaxing incisions in the Bowman's membrane (*Ophthalmic Surg.*, 15:225–229 (1984)).

There is a need in the field of ophthalmology for a reliable procedure whereby synthetic lenses for refractive correction can be permanently implanted and incorporated into the tissues of a patient's eye. Furthermore, there is a need generally for procedures whereby prosthetic devices can be permanently implanted and incorporated beneath epithelial tissues in humans or animals.

SUMMARY OF THE INVENTION

The present invention provides a method for implanting a prosthetic device beneath an epithelial layer. In accordance with the method of the invention, a portion of the epithelium is removed in the area of implantation, a contiguous region of epithelium being left intact. The surface of the prosthetic device to be implanted is coated with a composition comprising crosslinked or uncrosslinked fibronectin, or a biologically active fragment or analog of fibronectin. The surface of the prosthetic device is one which is capable of binding to fibronectin. The surface of the device can be constructed of a material such as collagen which is capable, without chemical modification, of binding fibronectin. It can also be constructed of a synthetic material which does not naturally bind fibronectin but which can be chemically modified to make it capable of binding fibronectin. The binding properties of the fibronectin cause the coated device to become affixed to the subepithelial tissue, although mechanical fixation by suturing or otherwise anchoring the lens into the subepithelial tissue may also be employed. The epithelial tissue from the contiguous area is then allowed to grow over and affix itself to the surface of the prosthetic device.

The method of the invention can be employed in any application in which it is desired to implant a prosthetic device permanently beneath epithelial tissues.

DETAILED DESCRIPTION OF THE INVENTION

In the method of the invention, the surface of the prosthetic device to be implanted is coated with a composition comprising crosslinked or uncrosslinked fibronectin, a biologically active fragment or an analog thereof. Fibronectin is a glycoprotein (4–5% carbohydrate) having a molecular weight of about 220,000 daltons, which exists in the form of a 440,000-dalton dimer. Fibronectin exists in a plasma-associated form and a cell-associated form. It can conveniently be isolated from plasma by the procedure described by Nishida et al., *Jap. J. Ophth.*, 26:4416-24 (1985). Fibronectin is also known by various other names, including cold-insoluble globulin, surface fibroblast antigen, cell surface protein, band 1, L1 band, band I, zeta-protein, major fibroblast glycoprotein, galactoprotein A, large external transformation sensitive protein (LETS), micro-fibrillar protein, cell attachment et al., *Mol. & Cell. Biochem.*, 29:103-125 (1980). Therecan also be employed, in the practice of the invention, biologically active fragments or analogs of fibronectin. For example, proteins having a high degree of amino acid sequence homology with fibronectin, such as vitronectin (Suzuki, S., *J. Biol. Chem.*, 259:15307-15314 (1984)) can be employed in place of fibronectin. Other analogs, including analogs produced by genetic engineering techniques, can be used, provided they have cell-attaching activity of the type displayed by native-sequence fibronectin. Suitable fibronectin fragments and methods of their preparation are disclosed in U.S. Pat. No. 4,589,881, issued to Piersbacher and Ruoslahti, and U.S. Pat. No. 4,578,079, issued to Ruoslahti and Piersbacher, the disclosures of which are incorporated herein by reference. U.S. Pat. No. 4,589,881 discloses on 11.5 kDal, 108-amino acid fragment of fibronectin having cell attachment activity as well as a 30-amino acid subfragment which has cell attachment activity. U.S. Pat. No. 4,578,079 discloses fragments and analogs thereof, having the formulae X-Arg-Gly-Asp-Thr-Y, X-Arg-Gly-Asp-Cys-Y and X-Arg-Gly-Asp-Ser-Y, wherein X is H or at least one amino acid residue and Y is COOH or at least one amino acid residue. As used hereinafter, the term "fibronectin" shall be understood to include biologically active fragments and analogs thereof "Fibronectin" also includes naturally derived materials and those prepared by recombinant DNA techniques.

Typically, fibronectin is available in stabilized compositions which contain albumin and sugar as stabilizers, and buffering and osmolality-controlling salts. The following lyophilized formulation exemplifies fibronectin compositions that may be used in the present invention:

| | |
|---|---|
| fibronectin | 60.0 mg. |
| albumin | 30.0 mg. |
| sucrose | 150.4 mg. |

| | |
|---|---|
| NaCl | 25.4 mg. |
| NaH$_2$PO$_4$.2H$_2$O | 3.3 mg. |
| Na$_2$HPO$_4$.12H$_2$O | 3.5 mg. |

The fibronectin can be employed, in the method of the invention, in the form of a solution which is prepared by mixing the above-described formulation with saline to obtain the desired concentration of fibronectin.

The fibronectin employed should be free of viral activity, such as hepatitis virus. Removal of hepatitis viral activity from fibronectin can be accomplished by the procedures set forth in U.S. Pat. No. 4,242,206 issued to Ohmura, et al., the dislcosure of which is incorporated herein by reference.

Fibronectin exhibits a number of properties which suit it for use in the method of the invention. It is known to play a key role in the organization of cells and extracellular matrices in growing tissue. It is chemotactic for fibroblasts and keratocytes, which play an important role in wound healing. Thus, the fibronectin promotes growth and cellular organization of epithelial tissue across the surface of the prosthetic device and causes fibroblasts or keratocytes to migrate into the area to promote wound healing.

Fibronectin can be applied to the surfaces of the prosthetic device in crosslinked or uncrosslinked form. In the former case, the coating composition which is applied to the surface also contains a crosslinking agent. The crosslinking agent can be any crosslinking agent which is capable of crosslinking protein molecules through their amino acid side chains.

The crosslinking agent can be any compound which is capable of covalently crosslinking protein molecules and which is pharmaceutically acceptable for the intended application. Examples of such compounds include aldehydes, e.g. formaldehyde and glutaraldehyde; di-imidates, e.g., dimethyl adipimidate and dimethyl pimelimidate; water soluble di-N-hydroxysuccinimide esters, e.g., bis (sulfosuccinimidyl) suberate and disuccinimidyl tartarate; photoreactive crosslinking agents, e.g. p-azidophenyl glyoxal, N-hydroxysuccinimidyl-4-azidobenzoate and methyl-4-azidobenzoate; and heterobifunctional crosslinking agents, e.g. N-succinimidyl(4-iodoaetyl)aminobenzoate and succinimidyl-4-(N-maleimidomethyl) cyclohexane-1-carboacylate. Other classes of compounds that are known to crosslink proteins and that are pharmaceutically acceptable for the intended application can be employed.

Crosslinking agents evaluated are those of the diimidate ester class. These compounds can be defined by the formula:

(I)

wherein R is moiety such as —(CH$_2$)$_n$—, —S—S—, and —(CH$_2$)$_n$S—S—(CH$_2$)$_n$— in which n is an integer of 1 or greater, preferably not more than about 20; R' and R", which can be the same or different, are each alkoxy having from 1 to about 20 carbon atoms; and X$^-$ is an anionic counterion such as Cl$^-$ or Br$^-$. When R is —(CH$_2$)$_n$—S—S—(CH$_2$)$_n$—, n is preferably 2. One can mention, as exemplary of the di-imidate compounds, dimethyl pimelimidate dihydrochloride, dimethyl adipimidate dihydrochloride and dimethyl-3,3'-dithiobispropionimidate dihydrochloride.

The compound of formula I is preferably employed in the form of a solution at a pH at which the compound of formula I is capable of effecting crosslinking of protein molecules. Preferably, the solution is somewhat alkaline. In order to be ophthalmologically acceptable, the solution should not have a pH greater than about 8.5. Preferably, the compound of formula I is applied in a solution having a pH between about 7.5 and 8.5, most preferably about 7.8. Any suitable, ophthalmologically acceptable carrier material can be employed. For example, the compound of formula I can be provided in a 0.3 m solution of NaOH in sterile water, having a pH between 13.0 and 14.0, can be admixed with 50 mg/ml of the compound of formula II to yield a solution having a pH between 7.5 and 8.5, which is useful in the method of the invention.

The crosslinking agent evaluated is dimethyl pimelimidate dihydrochloride, which is the compound of the formula:

(II)

Dimethyl pimelimidate dihydrochloride has been used extensively as a fixative in histology applicatons.

Optionally, the materials which exhibit beneficial effects in wound healing, such as by providing a matrix for cell migration and growth, may also be incorporated into the coating composition. These are preferably extracellular matrix proteins (ECM's). ECM's are proteins which can be found in extracellular matrix structures laid down by cultured cells (Hsieh, P. and Baum, J., Invest. Ophth. & Vis. Sci., 26:457–463 (1985)). They are generally high molecular weight (>150,000 daltons) fibrinous glycoproteins, which include collagens, vitronectin, elastin, laminin, actin and fibrinogen. It is to be understood that reference herein to ECM materials includes not only materials isolated from their natural sources, but also, materials produced synthetically, by means of expression in genetically engineered microorganisms or a combination of both. In the case of proteins or glycoproteins, such materials shall include biologically active fragments and analogs of such proteins or glycoproteins. ECM materials other than fibronectin can be applied to the prosthetic device by treating it with a solution containing from about 0.1 mg/dl to 100 mg/dl of the material.

If desired, the coating composition can also contain medicaments and/or other materials which promote wound healing. For example, an antibiotic material can be dispersed in the coating composition. Suitable antibiotics include, by way of example, gentamicin, neomicin, bacitracin, and the like. In addition, other antimicrobial agents, antiviral agents, antiinflammatory agents, antiprotease agents hormones, vitamins, analgesics, chelating agents, mitogenic agents and the like may be incorporated into the coating composition.

Any of the known tissue growth factors can be dispersed in the coating composition. Growth factors are mitogenic proteins or polypeptides which promote cell proliferation. A number of growth factors are known. These include epidermal growth factor (EGF), transforming growth factor (TGF's) and nerve growth factor (NGF). Insulin, a polypeptide hormone, has mitogenic activity and can be used in conjunction with prostaglandin $F_2$, a non-peptide which has been shown to increase greatly the mitogenic activity of insulin (see Jimenez de Asua, L. et al., *Cold Spring Harbor Conf. Cell Proliferation*, Vol. 6, Sato, ed., Cold Spring Harbor Labs., New York [1979], at 403–424). Similar activation of insulin has been reported with fibroblast growth factor by Rudland, P. S. et al., *Proc. Natl. Acad. Sci., U.S.A.*, 76:1279–1293 (1974). Positive effects on cell growth have been demonstrated for platelet-derived growth factor or fibroblast-derived growth factor in combination with members of the insulin family such as somatomedins A and C (Stiles, C. D. et al., *Proc. Natl. Acad. Sci., U.S.A.*, 76:1279–1283 [1979]). Additionally, many new peptide growth factors have been isolated and characterized recently, as indicated in *Tissue Growth Factors*, R. Baserga, ed., Springer-Verlag pub., New York (1981). Other medicaments or growth factors are dispersed in the composition in known effective amounts.

As previously indicated, the fibronectin-containing coating composition can be applied to the surface of a prosthetic device in which the surface of the device is capable, with or without chemical modification, of binding fibronectin. Fibronectin contains binding regions which are capable of binding a number of proteins including collagen. Thus, for example, in the case of a prosthetic cornea containing collagen, as described in U.S. Pat. No. 4,581,030, issued to Bruns et al. or U.S. Pat. No. 4,223,984, issued to Miyata et al., it is not necessary to modify the surface chemically prior to treatment with the fibronectin-containing coating composition.

Most prosthetic devices, however, are not constructed of materials that are normally bound by fibronectin, but rather, of synthetic polymeric materials which can be modified chemically to make them bind fibronectin. Soft contact lenses, for example, are generally prepared from hydrogel materials.

In general, these types of polymers are prepared from hydrophilic monomers that can be copolymerized with other materials which impart desirable physical characteristics. In addition, polymerizable additives, such as UV-absorbing agents, can be added to impart desired properties to the finished articles. Contact lenses which can be implanted using the method of the invention are widely available and are made from a variety of materials. Examples of these types of hydrogels are polymers of 2-hydroxyethylacrylate (e.g., polymacon), various copolymers of 2-hydroxyethylmethacrylate (e.g., hafilcon A and B, vifilcon A, tetrafilcon, dimefilcon, bufilcon, perfilcon, etc.), copolymers of N-vinylpyrrolidone (e.g., lidofilcon A and B, scafilcon A, surfilcon, vifilcon, filcon YA, etc.), hydrophilic copolymers of acrylonitrile such as HYPAN, hydrogels containing collagen, for example, as described in U.S. Pat. Nos. 4,452,925 and 4,388,428 and *P.N.A.S., USA*, 77 (No. 4), 2064–2068 (1980). As used herein, the term "soft contact lens" is intended to include lenses made from the above-mentioned materials, and which have a high degree of permability to oxygen, nutrients (especially glucose) and to metabolites. The oxygen permability is at least as high as that of hydrogel lenses having water contents of about 70%. The permability to nutrients and metabolities is at least as high as that of hydrogel lenses having water contents of about 60% or effective pore sizes greater than about 12 Angstroms. In addition, these lenses should have good dimensional stability over a pH range of about 6.5 to 8, a temperature range of about 30° to 40° C. and an osmolarity range of about 50–400 mosn/kg.

In the case of prosthetic devices which do not normally bind fibronectin, the surfaces of the devices are modified to render them capable of binding fibronectin. One suitable method for modifying polymeric surfaces is by coating them with poly(L-lysine). Other polyamines, such as polyethyleneimine, polyallylamine, etc., can also be used. While the precise mechanism of attachment is not understood, homopolymers of the amino acid L-lysine are capable of binding to a wide variety of polymers. The molecular weight of the poly(L-lysine) is not particularly critical. Poly(L-lysine) having molecular weights from 30,000 daltons to greater than 300,000 daltons have been successfully employed to treat the surfaces of prosthetic devices to render them capable of binding fibronectin. A preferred method of pretreating the surface comprises incubating it in an aqueous solution of poly(L-lysine) for a period from about 1 hr. to 24 hrs. at a temperature from about 15° C. to 30° C. The surface is then rinsed with sterile water.

Other methods which are known in the art to render normally unreactive surfaces reactive can also be employed to pretreat the prosthetic device. For example, a method of rendering the surface of a synthetic material capable of binding fibronectin comprises treating the surface with cyanogen bromide.

After the surface has been treated to render it capable of binding fibronectin, the fibronectin coating composition can be applied to the surface. If uncrosslinked fibronectin is to be applied to the surface, then the pretreated surface is incubated in a solution of fibronectin and, optionally, other materials such as ECM's and/or growth factors and/or medicaments. The solution can be an aqueous solution, e.g., sterile water solution, or it can be a solution in dimethyl formamide or other pharmaceutically acceptable non-toxic solvent. The fibronectin is generally present in the solution at a concentration from about 0.1 mg/ml to about 100 mg/ml, preferably from about 1 mg/ml to 10 mg/ml. Since fibronectin precipitates out of solution at low temperatures, it is preferred to incubate in a fibronectin solution at a temperature of at least about 15° C., preferably at room temperature. Time of incubation is from about ¼ hr. to 24 hrs.

Preferably, the fibronectin-containing coating composition is applied in the form of a crosslinked coating. In a preferred embodiment, a crosslinking agent as previously described, e.g., dimethyl pimelimidate dihydrochloride is first applied to the pretreated surface of the prosthetic device. This can be accomplished by incubating the surface in an aqueous solution of crosslinking agent. The crosslinking agent binds to the pretreated surface. In the case of a poly(L-lysine) pretreated surface, the poly(L-lysine) binds the polymeric surface of the prosthetic device and the crosslinking agent then binds to the poly(L-lysine). Since the crosslinking agent is multifunctional, it can bind to the poly(L-lysine) and still have functional groups available to react with fibronectin. Preferably, the prosthetic device is incubated with a solution of crosslinking agent having a concentration from about 1 mg/ml to about 20 mg/ml for a period from about ½ hr. to 1½ hrs. It is preferred to carry out the incubation at a temperature from about 1° C. to 25° C.

After incubating the pretreated prosthetic device in crosslinking agent, the surface is then rinsed with sterile water and treated with fibronectin by incubating it in a solution of fibronectin, which optionally can contain other materials, such as ECM's, growth factors and medicaments. The solvents, fibronectin concentrations, incubation time and temperature can be as previously described for the application of an uncrosslinked fibronection coating. The fibronectin and, optionally, other ECM materials, growth factors or medicaments react with the crosslinking agent to form a crosslinked coating which is bound to the surface of the prosthetic device.

In an alternative embodiment, a composition containing fibronectin, a crosslinking agent and, optionally, other ingredients such as ECM's or growth factors or medicaments, is first formed into a crosslinked gel. This can be accomplished by dissolving the ingredients in a suitable medium such as phosphate buffered saline, pouring the mixture into a thin film and allowing the fibronectin to crosslink to form a gel in the form of a thin film. The film can then be cut into an appropriate configuration to be applied to the surface of the prosthetic device. In preparing the film, the ratio of fibronectin to crosslinking agent can vary over a fairly wide range and is not narrowly critical. For example, gels can be produced using weight ratios of fibronectin to crosslinker from about 5:1 to 1:4. However, at ratios exceeding 1:1, the gel may be somewhat more rigid than is optimally desirable. Again, if the prosthetic device is made of a synthetic material which does not normally bind fibronectin, then the surface of the prosthetic device will have been pretreated to render it capable of binding fibronectin.

Figure 1:
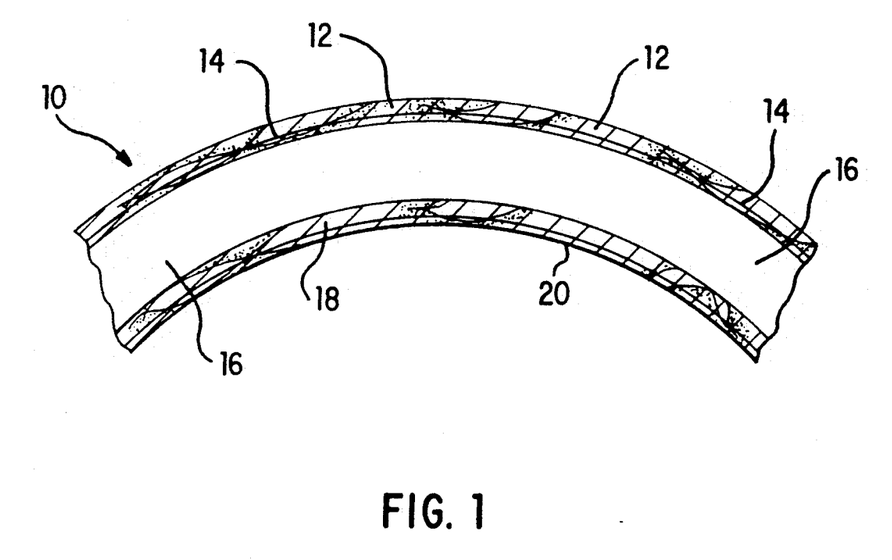
FIG. 1 illustrates a cross-section of a portion of an intact human cornea.
Figure 2:
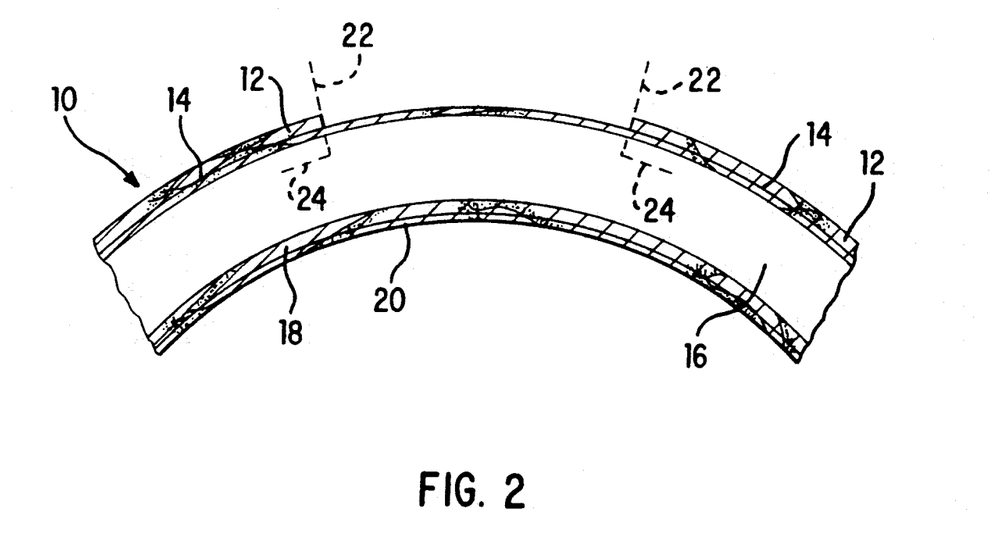
FIG. 2 illustrates a cross-section of a portion of a human cornea which has been prepared for implantation of a surface modified soft contact lens.
Figure 3:
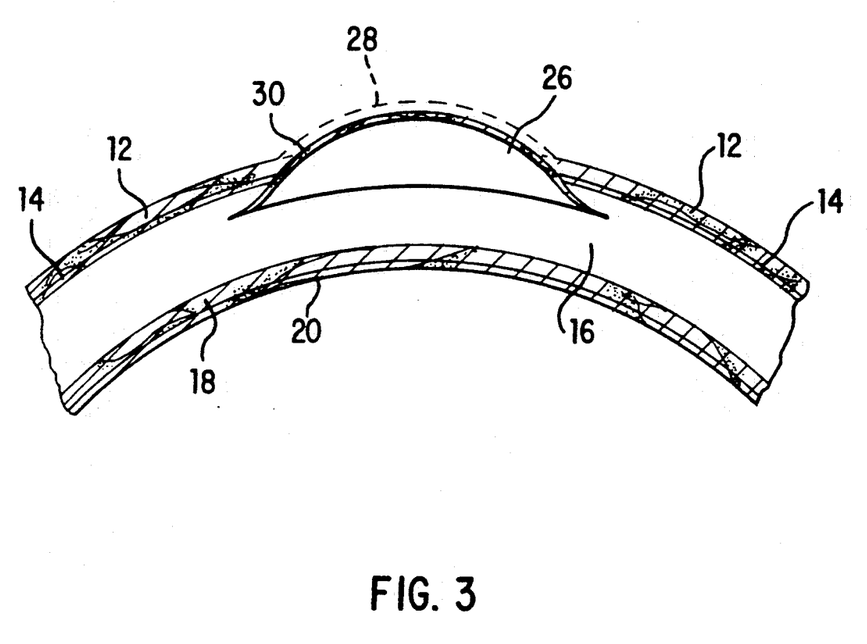
FIG. 3 represents a cross-section of a portion of a human cornea containing an implanted lens.

A preferred embodiment of the invention, in which the method of the invention is used to implant a soft contact lens permanently in the cornea, can be understood with reference to FIGS. 1, 2 and 3.

FIG. 1 illustrates a cross-section of a portion of an intact human cornea. The cornea 10 is made up of a series of layers. The anterior layer, known as the epithelium 12, serves the function of maintaining the integrity of the cornea. Epithelial cells are rich in glycogen, enzymes and acetylcholine and their activity regulates the corneal corpuscles and controls the transport of water and electrolytes through lamellae of the stroma 16. Beneath the epithelium 12 is the Bowman's membrane 14, which separates the epithelium 12 from the stroma 16, which is the thick portion of the cornea. Descemet's membrane 18 separates the stroma 16 from the endothelium 20, which is a single layer of cells forming the posterior surface of the cornea 10.

FIG. 2 represents a cross-section of a portion of a human cornea which has been prepared for implantation of a soft contact lens according to the method of the invention. To prepare the cornea for implantation, a circular portion of the epithelium 12 is first removed from the center of the cornea. Alternatively, all or part of the epithelium may be removed intact and replaced following implantation, as described by Martel, J. R. and Aguayo-Martel, J, *Ophthalmology Times*, Aug. 1, 1987. A suitable method for removing epithelial tissue is by applying a sterile solution of cocaine to the area. Treatment with cocaine degrades the epithelial tissue, but does not damage the Bowman's membrane 14. FIG. 2 illustrates a cross-section of a cornea 10 in which a central portion of the epithelium 12 has been removed, leaving the epithelium 12 intact in the surrounding area. Following removal of degraded epithelial tissue by sponging, an incision, indicated by a dotted line 22, is made using a trefine. The incision is made through the Bowman's membrane 14 approximately 0.1 mm into the stromal tissue 16. The incision extends in a circular path peripherally around the area into which the contact lens is to be inserted. Using a tissue spreader the surgeon then forms a continuous pocket, indicated by dotted line 24, which extends radially outward into the stromal tissue 16 in order to form a flap of tissue around the periphery of the implantation site.

FIG. 3 represents a cross-section of a portion of a human cornea containing an implanted contact lens 26. The lens 26 is a soft contact lens which has been treated on its anterior and posterior surfaces by pretreatment with poly(L-lysine), followed by application of a coating 30 comprising fibronectin crosslinked with dimethyl pimelimidate dihydrochloride, using the previously described coating procedures. The anterior surface of the contact lens 26 is appropriately shaped, by procedures known in the art, to provide refractive correction to the patient. The posterior surface of the contact lens 26 is shaped to conform to the surface of the patient's cornea 10.

The coated lens 26 is inserted into the cornea 10 by placing the edge of the lens 26 into the pocket under the peripheral flap formed by incisions 22 and 24, making sure that the posterior surface of the lens 26 is flush with the surface of the Bowman's membrane 14. Advantageously, a solution of tissue adhesive or crosslinking agent is first applied between the stroma 16 and the posterior surface of the lens 26 to fix the lens in place. After insertion of the lens 26, the surgeon lifts the edge of the flap and inserts a small amount of an aqueous mixture of fibronectin and tissue adhesive or crosslinking agent into the pocket between the edge of the lens 26 and the flap. The fibronectin will then become crosslinked and bind the stromal tissue to the edge of the lens 26, forming an occlusive seal.

The fibronectin-containing coating 30 on the posterior surface of the lens 26 acts to bind the surface of the Bowman's membrane 14 to the lens surface, thereby fixing the position of the contact lens 26 on the cornea 10. A major advantage of the method of the invention for implanting contact lenses is that it may not require stitching the lens in place or using other mechanical means of fixation. The coating 30 acts to promote wound healing as well as to bind the lens to the corneal surface. The key function of the fibronectin-containing coating 30 on the anterior surface of the implanted contact lens 26 is to promote the migration of epithelial cells from the contiguous epithelium 12 across the surface of the lens 26 in order to form a new epithelial surface, indicated by dotted line 28, on the surface of the lens. In primate studies, we have found that the newly formed epithelium 28 completely covers the implanted lens 26 within several days after insertion. The newly formed epithelium 28 regulates the transport of fluids and gases to and from the implanted lens 26.

In some instances, due to injury or disease, it is necessary to remove not only a portion of the epithelium 12, but also a portion of the Bowman's membrane and a portion of the stroma 16 prior to implantation of an ophthalmic prosthesis. In such "deep stromal" implants there is a danger that the cornea may re-epithelialize beneath the implanted prosthesis, which is unacceptable. In such cases, the wound bed can be prepared by preforming a thin sheet of crosslinked fibronectin and tissue adhesive or crosslinking agent and inserting an appropriately configured sheet of the crosslinked material into the wound bed prior to implantation of the prosthesis. The sheet of fibronectin not only serves to raise the prosthesis closer to the corneal surface and to adhere the prosthesis to the stroma, but also promotes regeneration of stromal tissue beneath the prosthesis and inhibits epithelialization beneath the prosthesis.

The following examples are intended to illustrate further the practice of the invention and is not intended to limit its scope in any way.

EXAMPLE

A hydrophilic lens prepared from a copolymer containing N-vinylpyrrolidone is soaked overnight at room temperature in 1.5 ml. of aqueous solution containing 2 mg/ml of poly(L-lysine). The lens is then rinsed in water and soaked for 30 minutes at 4° C. in a 0.9N saline solution containing 10 mg/ml dimethylpimelimidate dihydrochloride. The lens is then rinsed in water and then soaked for 2 hours at room temperature in an aqueous solution containing about 50 mg/ml fibronectin. The lens is then rinsed in water and soaked in a 0.9% saline solution containing 10 mg/ml dimethylpimelimidate dihydrochloride at room temperature for 1 hour. The lens is then rinsed in water and implanted using standard surgical techniques as previously described for epikeratophakia, except that the lens is glued in place using fibronectin and dimethylpimelimidate dihydrochloride. Typically, re-epithelialization occurs within a week.

What is claimed is:

1. A treated corneal prosthetic device for subepithelial implantation in a human or animal cornea comprising a prosthetic device having on its surface a coating comprising crosslinked or uncrosslinked fibronectin or a biologically active fragment or analog of fibronectin, the surface of the prosthetic device comprising a synthetic polymeric material which is pre-treated to chemically modify said material to make it capable of binding said fibronectin, fragment or analog, whereby the coating is supportive for corneal epithelial cells and supports the attachment, growth and migration of corneal epithelial tissues across the surface of the prosthetic device.

2. A device as claimed in claim 1 wherein the surface of the synthetic polymeric material is pretreated by coating with poly(L-lysine) to render it capable of binding fibronectin.

3. A device as claimed in claim 1 wherein the coating is a crosslinked coating comprising fibronectin and a crosslinking agent capable of crosslinking fibronectin.

4. A device as claimed in claim 3, wherein the crosslinking agent is a compound of the formula wherein R is selected from $-CH_2-_n$, $-S-S-$, and $-(CH_2)_n-S-S-(CH_2)_n-$ which n, is an integer having a value of at least 1; R' and R", which can be the same or different are each individually alkoxy having from 1 to 20 carbon atoms; and $X^-$ is an anionic counterion.

5. A device as claimed in claim 4 wherein the crosslinking agent is dimethyl pimelimidate dihydrochloride.

6. A device as claimed in claim 1 wherein the surface of the synthetic polymeric material is pretreated with cyanogen bromide to render it capable of binding fibronectin.

7. A treated corneal prosthetic device for subepithelial implantation in a human or animal cornea comprising a prosthetic device having on its surface a coating comprising crosslinked or uncrosslinked fibronectin, the surface of the prosthetic device comprising a synthetic polymeric material which is pre-treated to chemically modify said material to make it capable of binding said fibronectin, whereby the coating is supportive for corneal epithelial cells and supports the attachment, growth and migration of corneal epithelial tissues across the surface of the prosthetic device.

* * * * *

UNITED STATES PATENT AND TRADEMARK OFFICE
CERTIFICATE OF CORRECTION

PATENT NO. : 5,171,318

DATED : December 15, 1992

INVENTOR(S) : David Gibson et al.

It is certified that error appears in the above-identified patent and that said Letters Patent is hereby corrected as shown below:

Col. 12, line 18, "—$CH_2$—$_n$" should be -- $(CH_2)_n$ --.

Col. 12, line 26 "$(CH_2)_n$S—S—$CH_2)_n$" should be -- $(CH_2)_n$S—S$(CH_2)_n$ --

Signed and Sealed this

Eighteenth Day of January, 1994

Attest:

BRUCE LEHMAN

Attesting Officer     Commissioner of Patents and Trademarks